United States Patent
Miyachi

(10) Patent No.: US 11,766,241 B2
(45) Date of Patent: Sep. 26, 2023

(54) ULTRASOUND SYSTEM IN WHICH AN ULTRASOUND PROBE AND A DISPLAY DEVICE ARE WIRELESSLY CONNECTED WITH EACH OTHER AND METHOD FOR CONTROLLING ULTRASOUND SYSTEM IN WHICH AN ULTRASOUND PROBE AND A DISPLAY DEVICE ARE WIRELESSLY CONNECTED WITH EACH OTHER

(71) Applicant: FUJIFILM Corporation, Tokyo (JP)

(72) Inventor: Yukiya Miyachi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/062,692

(22) Filed: Oct. 5, 2020

(65) Prior Publication Data

US 2021/0015460 A1 Jan. 21, 2021

Related U.S. Application Data

(63) Continuation of application No. PCT/JP2019/017933, filed on Apr. 26, 2019.

(30) Foreign Application Priority Data

Apr. 27, 2018 (JP) .................................. 2018-086842

(51) Int. Cl.
*A61B 8/00* (2006.01)
*A61B 8/08* (2006.01)

(52) U.S. Cl.
CPC .......... *A61B 8/4472* (2013.01); *A61B 8/4494* (2013.01); *A61B 8/461* (2013.01); *A61B 8/5246* (2013.01)

(58) Field of Classification Search
CPC ..... A61B 8/4472; A61B 8/4494; A61B 8/461; A61B 8/5246; G01S 15/8995; G01S 7/52085

See application file for complete search history.

(56) References Cited

U.S. PATENT DOCUMENTS 6,113,547 A * 9/2000 Catallo .................. G01S 7/003
600/459
6,142,946 A * 11/2000 Hwang ................ A61B 8/4472
600/459

(Continued)

FOREIGN PATENT DOCUMENTS

EP 2 829 234 A2 1/2015
JP 2005-304749 A 11/2005

(Continued)

OTHER PUBLICATIONS

JP-2008018107-A (Year: 2008).*

(Continued)

*Primary Examiner* — Joel Lamprecht
*Assistant Examiner* — Nyrobi Celestine
(74) *Attorney, Agent, or Firm* — Studebaker & Brackett PC

(57) ABSTRACT

An ultrasound system includes an ultrasound probe and an image display device. The ultrasound probe includes a transducer array, a transmitting and receiving unit that transmits and receives ultrasonic waves using the transducer array to generate a sound ray signal; a frame image information data generation unit that generates frame image information data from the sound ray signal; and a wireless communication unit that transmits a plurality of frame image information data items to the image display device. The image display device includes a frame type determination unit that determines frame types of the plurality of frame image information data items, a combination determination unit that determines whether or not to combine the frame image information data items on the basis of the frame types, a compound image data generation unit that combines the plurality of frame image information data items, and a display unit that displays a compound image.

12 Claims, 6 Drawing Sheets

(56) References Cited

U.S. PATENT DOCUMENTS

| | | | |
|---|---|---|---|
| 6,224,552 B1* | 5/2001 | Jago | G01S 7/52057 600/443 |
| 8,506,488 B2* | 8/2013 | Shin | G01S 15/8995 600/443 |
| 2004/0015079 A1* | 1/2004 | Berger | A61B 18/02 600/437 |
| 2005/0004458 A1* | 1/2005 | Kanayama | G01N 29/0672 600/437 |
| 2005/0248587 A1 | 11/2005 | Kamiyama et al. | |
| 2009/0312643 A1* | 12/2009 | Ikegame | A61B 8/4455 600/459 |
| 2011/0077520 A1* | 3/2011 | Osawa | A61B 8/4483 600/443 |
| 2011/0077522 A1* | 3/2011 | Sato | G01S 15/8995 600/447 |
| 2011/0105904 A1 | 5/2011 | Watanabe | |
| 2012/0123271 A1* | 5/2012 | Cai | A61B 8/464 600/454 |
| 2012/0232396 A1 | 9/2012 | Tanabe | |
| 2012/0330155 A1* | 12/2012 | Jiang | A61B 8/08 600/438 |
| 2013/0128691 A1* | 5/2013 | Martins | G01S 15/8995 367/7 |
| 2013/0245445 A1 | 9/2013 | Kakee et al. | |
| 2013/0258805 A1* | 10/2013 | Hansen | G01S 7/52046 367/8 |
| 2013/0261432 A1* | 10/2013 | Guo | A61B 8/5207 600/424 |
| 2014/0148699 A1 | 5/2014 | Shim et al. | |
| 2015/0032004 A1* | 1/2015 | Kim | A61B 8/4472 600/443 |
| 2015/0196278 A1* | 7/2015 | Noguchi | A61B 8/54 600/447 |
| 2016/0113632 A1* | 4/2016 | Ribes | A61B 8/5269 600/440 |
| 2016/0338664 A1 | 11/2016 | Misono | |
| 2018/0017669 A1* | 1/2018 | Lee | A61B 8/145 |
| 2018/0070914 A1* | 3/2018 | Yang | A61B 8/4405 |
| 2019/0223841 A1 | 7/2019 | Miyazawa et al. | |
| 2019/0369240 A1* | 12/2019 | Gan | G01S 15/8995 |

FOREIGN PATENT DOCUMENTS

| | | |
|---|---|---|
| JP | 2008018107 A * | 1/2008 |
| JP | 2013-215559 A | 10/2013 |
| JP | 2015-211726 A | 11/2015 |
| JP | 2016-502442 A | 1/2016 |
| JP | 2018-057696 A | 4/2018 |
| WO | 2016/098429 A1 | 6/2016 |

OTHER PUBLICATIONS

The extended European search report issued by the European Patent Office dated Mar. 9, 2021, which corresponds to European Patent Application No. 19793223.9-1126 and is related to U.S. Appl. No. 17/062,692.

International Search Report issued in PCT/JP2019/017933; dated Jul. 16, 2019.

Written Opinion issued in PCT/JP2019/017933; dated Jul. 16, 2019.

* cited by examiner

ULTRASOUND SYSTEM IN WHICH AN ULTRASOUND PROBE AND A DISPLAY DEVICE ARE WIRELESSLY CONNECTED WITH EACH OTHER AND METHOD FOR CONTROLLING ULTRASOUND SYSTEM IN WHICH AN ULTRASOUND PROBE AND A DISPLAY DEVICE ARE WIRELESSLY CONNECTED WITH EACH OTHER

CROSS-REFERENCE TO RELATED APPLICATIONS

This application is a Continuation of PCT International Application No. PCT/JP2019/017933 filed on Apr. 26, 2019, which claims priority under 35 U.S.C. § 119(a) to Japanese Patent Application No. 2018-086842 filed on Apr. 27, 2018. The above application is hereby expressly incorporated by reference, in its entirety, into the present application.

BACKGROUND OF THE INVENTION

1. Field of the Invention

The present invention relates to an ultrasound system and a method for controlling the ultrasound system, and more particularly, to an ultrasound system in which an ultrasound probe and an image display device are wirelessly connected to each other and a method for controlling the ultrasound system.

2. Description of the Related Art

In the related art, an ultrasound diagnostic apparatus using an ultrasound image has been put to practical use in the medical field. In general, this type of ultrasound diagnostic apparatus includes an ultrasound probe having a transducer array provided therein and an apparatus main body connected to the ultrasound probe. Ultrasonic waves are transmitted from the ultrasound probe to a subject. The ultrasound probe receives ultrasound echoes from the subject. The apparatus main body electrically processes a reception signal to generate an ultrasound image.

In recent years, for example, as disclosed in JP2015-211726A, an ultrasound system has been developed in which an ultrasound probe and an apparatus main body are connected by wireless communication to improve the operability and mobility of the ultrasound probe.

In the wireless ultrasound system, an analog reception signal output from the transducer array of the ultrasound probe is transmitted to the apparatus main body by wireless communication. Alternatively, a circuit for signal processing is provided in the ultrasound probe and the ultrasound probe performs digital processing on the reception signal output from the transducer array and transmits the reception signal to the apparatus main body using wireless communication. The apparatus main body generates an ultrasound image.

SUMMARY OF THE INVENTION

However, in general, in an ultrasound system, an image obtained by combining ultrasound images of a plurality of frames, such as a so-called spatial compound image, may be displayed on a display unit. In the case of a wireless ultrasound system in which an ultrasound probe and an image display device are connected to each other by wireless communication and ultrasound images are combined in the image display device, there is a concern that the wireless transmission of data acquired by the ultrasound probe will not be normally performed due to the deterioration of a wireless communication state, such as the interruption of the wireless communication between the ultrasound probe and the image display device, images will not be normally combined, and a compound image will not be normally displayed in the image display device.

The invention has been made in order to solve the problems of the related art and an object of the invention is to provide an ultrasound system that can normally display a compound image regardless of a wireless communication state between an ultrasound probe and an image display device and a method for controlling the ultrasound system.

In order to achieve the above object, according to the invention, there is provided an ultrasound system comprising an ultrasound probe and an image display device that are wirelessly connected to each other. The image display device displays a compound image on the basis of a plurality of frame image information data items generated by the ultrasound probe. The ultrasound probe includes: a transducer array; a transmitting and receiving unit that performs transmission and reception of ultrasonic waves on the basis of a transmission and reception sequence using the transducer array to generate a sound ray signal; a frame image information data generation unit that generates the plurality of frame image information data items on the basis of the sound ray signal generated by the transmitting and receiving unit; and a wireless communication unit that sequentially wirelessly transmits the plurality of frame image information data items generated by the frame image information data generation unit to the image display device. The image display device includes: a frame type determination unit that determines a frame type of each of the plurality of frame image information data items wirelessly transmitted through the wireless communication unit of the ultrasound probe; a combination determination unit that determines whether or not to combine the plurality of frame image information data items on the basis of each of the frame types determined by the frame type determination unit; a compound image data generation unit that combines the plurality of frame image information data items determined to be combined by the combination determination unit to generate compound image data; and a display unit that displays the compound image on the basis of the compound image data generated by the compound image data generation unit.

The ultrasound probe may include a header information attachment unit that attaches header information to each of the plurality of frame image information data items generated by the frame image information data generation unit, and the frame type determination unit of the image display device may determine the frame type of each of the plurality of frame image information data items on the basis of the header information attached by the header information attachment unit.

In this case, the header information may include frame numbers that are sequentially given to the plurality of frame image information data items, and the frame type determination unit may determine the frame types on the basis of the frame numbers of the plurality of frame image information data items and the transmission and reception sequence in the transmitting and receiving unit of the ultrasound probe.

Alternatively, the header information may include a generation time of each of the plurality of frame image information data items by the frame image information data generation unit, and the frame type determination unit may determine the frame type on the basis of the generation time of each of the plurality of frame image information data items and the transmission and reception sequence in the transmitting and receiving unit of the ultrasound probe.

Alternatively, the header information may include the frame type of each of the plurality of frame image information data items, and the frame type determination unit may read the frame type from the header information to determine the frame type.

Further, the frame type determination unit may analyze each of the frame image information data items to determine the frame type of the frame image information data.

In this case, the frame type determination unit may analyze data corresponding to a predetermined region of a shallow portion in the frame image information data to determine the frame type of the frame image information data.

Furthermore, in this case, preferably, the ultrasound probe includes an acoustic lens, and the data corresponding to the predetermined region is data generated on the basis of an ultrasound echo obtained by reflection of the ultrasonic waves transmitted from the transducer array from a front surface of the acoustic lens.

Further, the compound image data generation unit may combine the plurality of frame image information data items corresponding to a plurality of images having different steering angle ranges to generate the compound image data.

Alternatively, the compound image data generation unit may combine two frame image information data items corresponding to a fundamental wave image and a harmonic image to generate the compound image data.

Alternatively, the compound image data generation unit may combine two frame image information data items corresponding to a brightness mode image and a color Doppler image to generate the compound image data.

Alternatively, the compound image data generation unit may weight and add a plurality of frame image information data items that are continuous in time series to generate the compound image data.

Preferably, the frame image information data is a signal obtained by performing attenuation correction according to a depth of a reflection position of the ultrasonic waves and an envelope detection process on the sound ray signal generated by the transmitting and receiving unit.

In addition, the frame image information data may be an ultrasound image signal obtained by performing attenuation correction according to a depth of a reflection position of the ultrasonic waves and an envelope detection process on the sound ray signal generated by the transmitting and receiving unit and converting the sound ray signal according to a predetermined image display method.

Further, preferably, the transmitting and receiving unit includes: a transmitting unit that directs the transducer array to transmit the ultrasonic waves; and a receiving unit that generates the sound ray signal on the basis of a reception signal acquired by the transducer array.

According to the invention, there is provided a method for controlling an ultrasound system which includes an ultrasound probe and an image display device wirelessly connected to each other and in which the image display device displays a compound image on the basis of a plurality of frame image information data items generated by the ultrasound probe. The method comprises: performing transmission and reception of ultrasonic waves on the basis of a transmission and reception sequence using a transducer array of the ultrasound probe to generate a sound ray signal; generating the plurality of frame image information data items on the basis of the generated sound ray signal; sequentially wirelessly transmitting the plurality of generated frame image information data items from the ultrasound probe to the image display device; determining a frame type of each of the plurality of frame image information data items wirelessly transmitted from the ultrasound probe in the image display device; determining whether or not to combine the plurality of frame image information data items on the basis of each of the determined frame types; combining the plurality of frame image information data items determined to be combined to generate compound image data; and displaying the compound image on a display unit of the image display device on the basis of the generated compound image data.

According to the invention, the ultrasound system includes the frame type determination unit that determines the frame type of each of the plurality of frame image information data items wirelessly transmitted through the wireless communication unit of the ultrasound probe, the combination determination unit that determines whether or not to combine the plurality of frame image information data items on the basis of each frame type determined by the frame type determination unit, and the compound image data generation unit that combines the plurality of frame image information data items determined to be combined by the combination determination unit to generate the compound image data. Therefore, it is possible to normally display a compound image regardless of the wireless communication state between the ultrasound probe and the image display device.

DESCRIPTION OF THE PREFERRED EMBODIMENTS

Embodiments of the invention will be described below with reference to the accompanying drawings. In the invention, a compound image is generated on the basis of a plurality of image signals corresponding to ultrasound images of a plurality of frames.

Embodiment 1

Figure 1:
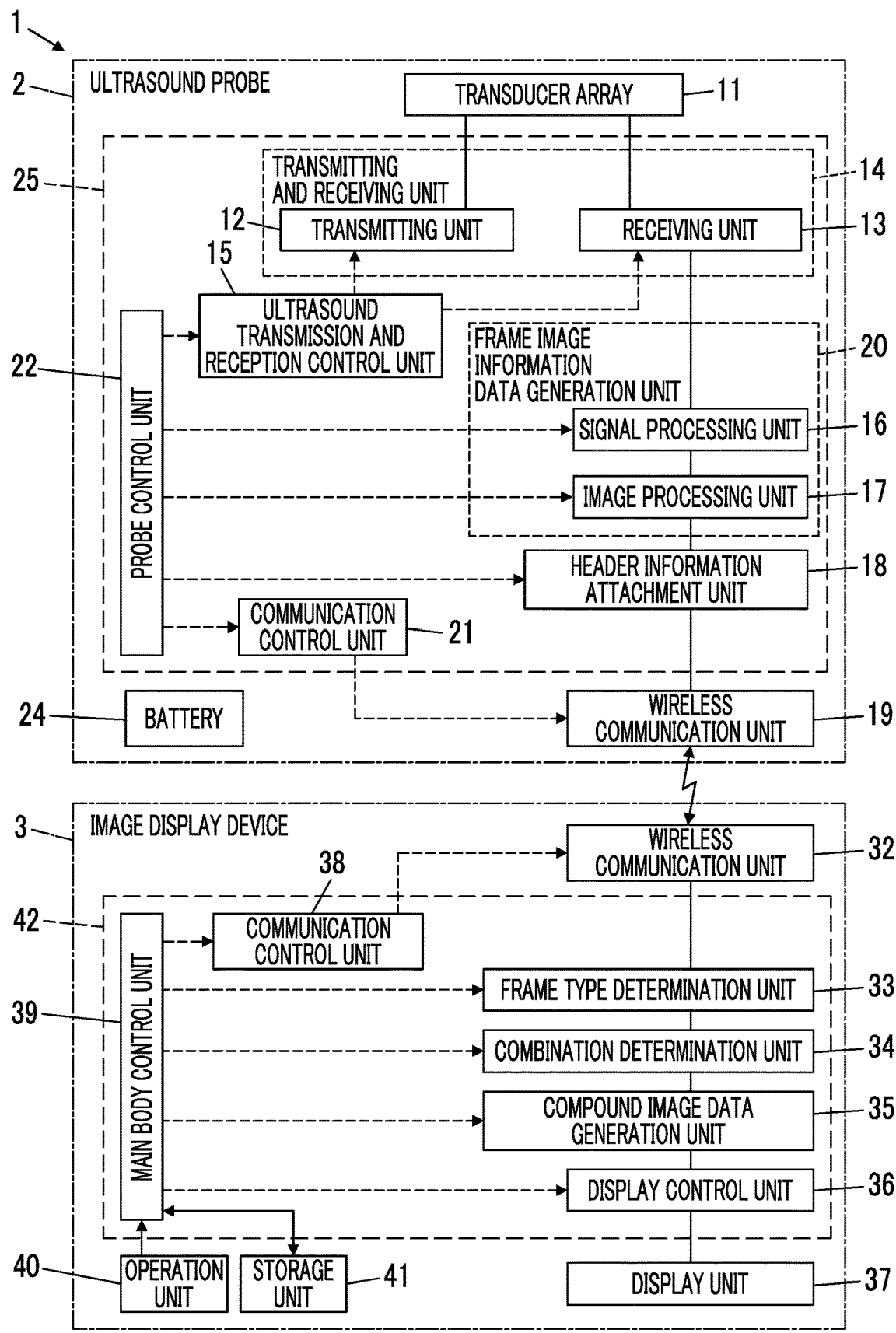
FIG. 1 is a block diagram illustrating a configuration of an ultrasound system according to Embodiment 1 of the invention.

FIG. 1 illustrates the configuration of an ultrasound system 1 according to Embodiment 1 of the invention. The ultrasound system 1 comprises an ultrasound probe 2 and an image display device 3. The ultrasound probe 2 and the image display device 3 are connected to each other by wireless communication.

The ultrasound probe 2 comprises a transducer array 11. The transducer array 11 is connected to a transmitting unit 12 and a receiving unit 13. The transmitting unit 12 and the receiving unit 13 form a transmitting and receiving unit 14. An ultrasound transmission and reception control unit 15 is connected to the transmitting unit 12 and the receiving unit 13. A signal processing unit 16, an image processing unit 17, and a header information attachment unit 18, and a wireless communication unit 19 are sequentially connected to the receiving unit 13. Here, a frame image information data generation unit 20 is configured by the signal processing unit 16 and the image processing unit 17.

A communication control unit 21 is connected to the wireless communication unit 19. A probe control unit 22 is connected to the ultrasound transmission and reception control unit 15, the signal processing unit 16, the image processing unit 17, the header information attachment unit 18, and the communication control unit 21. Further, the ultrasound probe 2 has a battery 24 provided therein.

Furthermore, a probe-side processor 25 is configured by the transmitting and receiving unit 14, the ultrasound transmission and reception control unit 15, the header information attachment unit 18, the frame image information data generation unit 20, the communication control unit 21, and the probe control unit 22.

The image display device 3 includes a wireless communication unit 32. A frame type determination unit 33, a combination determination unit 34, a compound image data generation unit 35, a display control unit 36, and a display unit 37 are sequentially connected to the wireless communication unit 32. Further, a communication control unit 38 is connected to the wireless communication unit 32. A main body control unit 39 is connected to the frame type determination unit 33, the combination determination unit 34, the compound image data generation unit 35, the display control unit 36, and the communication control unit 38. Furthermore, an operation unit 40 and a storage unit 41 are connected to the main body control unit 39. The main body control unit 39 and the storage unit 41 are connected such that information can be bidirectionally transmitted and received.

In addition, a display-device-side processor 42 is configured by the frame type determination unit 33, the combination determination unit 34, the compound image data generation unit 35, the display control unit 36, the communication control unit 38, and the main body control unit 39.

The transducer array 11 of the ultrasound probe 2 has a plurality of ultrasound transducers which are arranged one-dimensionally or two-dimensionally. Each of the transducers transmits ultrasonic waves according to a driving signal supplied from the transmitting unit 12, receives waves reflected from a subject, and outputs an analog reception signal. Each transducer is configured using an element in which electrodes are formed at both ends of a piezoelectric body consisting of, for example, a piezoelectric ceramic typified by lead zirconate titanate (PZT), a polymeric piezoelectric element typified by polyvinylidene difluoride (PVDF), and a piezoelectric single crystal typified by lead magnesium niobate-lead titanate (PMN-PT).

The ultrasound transmission and reception control unit 15 controls the transmitting unit 12 and the receiving unit 13 of the transmitting and receiving unit 14 to perform the transmission of ultrasound beams and the reception of ultrasound echoes on the basis of an inspection mode, a scanning method, and a predetermined transmission and reception sequence instructed by the probe control unit 22. Here, it is assumed that the inspection mode indicates any one of the inspection modes that can be used in an ultrasound diagnostic apparatus, such as a brightness (B) mode, a color Doppler (CF) mode, a power Doppler (PD) mode, a motion (M) mode, and a pulse Doppler (PW) mode, and the scanning method indicates any one of scanning methods, such as an electronic sector scanning method, an electronic linear scanning method, and an electronic convex scanning method.

The transmitting unit 12 of the transmitting and receiving unit 14 includes, for example, a plurality of pulse generators, adjusts the amount of delay of each driving signal on the basis of a transmission delay pattern selected according to a control signal from the ultrasound transmission and reception control unit 15 such that the ultrasonic waves transmitted from the plurality of transducers of the transducer array 11 form an ultrasound beam, and supplies the driving signals to the plurality of transducers. As such, in a case in which a pulsed or continuous-wave voltage is applied to the electrodes of the transducers of the transducer array 11, the piezoelectric body is expanded and contracted and pulsed or continuous ultrasonic waves are generated from each transducer. An ultrasound beam whose focus has been narrowed down on a certain scanning line is formed from a combined wave of the ultrasonic waves.

The transmitted ultrasound beam is reflected by a target, such as a part of the subject, and is propagated as a so-called ultrasound echo toward the transducer array 11. The ultrasound echoes propagated toward the transducer array 11 in this way are received by each of the ultrasound transducers forming the transducer array 11. In this case, each of the ultrasound transducers forming the transducer array 11 receives the propagated ultrasound echoes, is expanded and contracted to generate an electric signal, and outputs the electric signal to the receiving unit 13.

Figure 2:
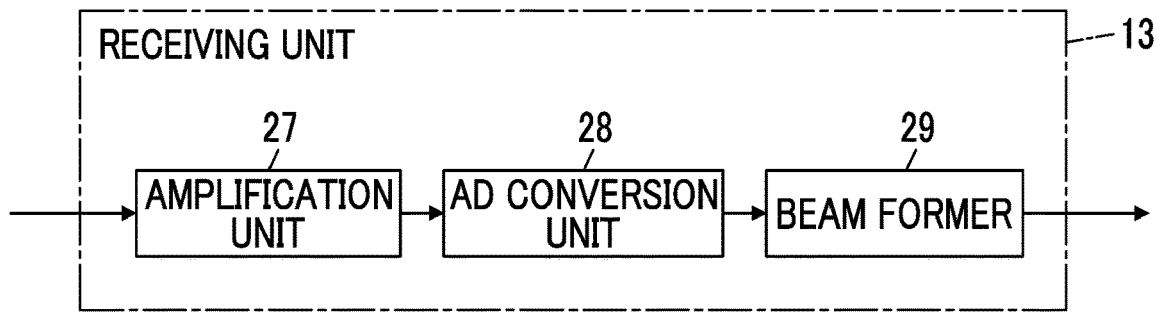
FIG. 2 is a block diagram illustrating an internal configuration of a receiving unit according to Embodiment 1 of the invention.

The receiving unit 13 of the transmitting and receiving unit 14 processes the reception signal output from the transducer array 11 according to a control signal from the ultrasound transmission and reception control unit 15. As illustrated in FIG. 2, the receiving unit 13 has a configuration in which an amplification unit 27, an analog digital (AD) conversion unit 28, and a beam former 29 are connected in series to each other. The amplification unit 27 amplifies the reception signal which is an analog signal input from each of the ultrasound transducers forming the transducer array 11 and transmits the amplified reception signal to the AD conversion unit 28. The AD conversion unit 28 converts the analog reception signal transmitted from the amplification unit 27 into a digital signal to acquire reception data, and transmits the reception data to the beam former 29. The beam former 29 performs a reception focusing process which gives a delay to each reception data item following a set sound velocity on the basis of a reception delay pattern selected according to a control signal from the ultrasound transmission and reception control unit 15 and performs addition (phasing addition). The sound ray signal in which the focus of the ultrasound echo is narrowed down on a certain scanning line is generated by the reception focusing process.

The frame image information data generation unit 20 of the probe-side processor 25 generates a plurality of frame image information data items on the basis of the sound ray signal generated by the beam former 29 of the receiving unit 13. The image display device 3 generates a compound image based on the plurality of frame image information data items, which will be described below.

Here, the signal processing unit 16 of the frame image information data generation unit 20 corrects the attenuation of the sound ray signal generated by the beam former 29 caused by a propagation distance according to the depth of the position where the ultrasonic waves are reflected and performs an envelope detection process on the sound ray signal to generate a signal which is tomographic image information of a plurality of frames related to the tissues in the subject for each frame unit.

The image processing unit 17 of the frame image information data generation unit 20 raster-converts the signal generated by the signal processing unit 16 into an image signal following a general television signal scanning method and performs various types of necessary image processing, such as brightness correction, gradation correction, sharpness correction, and color correction, on the generated image signal to generate ultrasound image signals corresponding to the tomographic images of a plurality of frames. In addition, the image processing unit 17 transmits the generated ultrasound image signals corresponding to the plurality of frames as frame image information data to the header information attachment unit 18.

The header information attachment unit 18 attaches header information, such as frame numbers, to each of the ultrasound image signals corresponding to the plurality of frames generated by the image processing unit 17 of the frame image information data generation unit 20 and transmits the ultrasound image signals corresponding to the plurality of frames to the wireless communication unit 19.

The wireless communication unit 19 of the ultrasound probe 2 includes an antenna for transmitting and receiving radio waves, modulates a carrier on the basis of the ultrasound image signals transmitted by the header information attachment unit 18 to generate transmission signals, supplies the transmission signals to the antenna, and transmits radio waves from the antenna, thereby wirelessly transmitting the ultrasound image signals corresponding to the plurality of frames in sequence. For example, amplitude shift keying (ASK), phase shift keying (PSK), quadrature phase shift keying (QPSK), and 16 quadrature amplitude modulation (16QAM) can be used as the carrier modulation method.

The communication control unit 21 of the probe-side processor 25 controls the wireless communication unit 19 such that the ultrasound image signal is transmitted with transmission radio field intensity set by the probe control unit 22.

The probe control unit 22 of the probe-side processor 25 controls each unit of the ultrasound probe 2 on the basis of, for example, a program stored in advance.

The battery 24 of the ultrasound probe 2 is provided in the ultrasound probe 2 and supplies power to each circuit of the ultrasound probe 2.

The wireless communication unit 32 of the image display device 3 includes an antenna for transmitting and receiving radio waves, receives the transmission signals transmitted by the wireless communication unit 19 of the ultrasound probe 2 through the antenna, demodulates the received transmission signals, and outputs the ultrasound image signals corresponding to the plurality of frames.

The communication control unit 38 of the display-device-side processor 42 controls the wireless communication unit 32 of the image display device 3 such that the transmission signals are received from the wireless communication unit 19 of the ultrasound probe 2.

The frame type determination unit 33 of the display-device-side processor 42 determines the frame type of each of the ultrasound image signals corresponding to the plurality of frames output from the wireless communication unit 32 of the image display device 3. Here, the frame type indicates the type of frame image information data for distinguishing each of the plurality of frame image information data items required to generate a compound image of one frame. For example, in a case in which a so-called spatial compound image obtained by combining N frame image information data items based on N different steering angle ranges is generated as the compound image, the frame type determination unit 33 can determine, as the frame types, the N steering angle ranges corresponding to the frame image information data items. Here, the steering angle range is an angle range in which scanning is performed along a scanning line of the ultrasound beams and the ultrasound echoes transmitted and received by the transmitting and receiving unit 14 of the probe-side processor 25. In addition, N is an integer equal to or greater than 2.

The combination determination unit 34 of the display-device-side processor 42 determines whether or not to combine the ultrasound image signals corresponding to a plurality of frames on the basis of each frame type determined by the frame type determination unit 33.

The compound image data generation unit 35 of the display-device-side processor 42 combines the ultrasound image signals corresponding to the plurality of frames determined to be combined by the combination determination unit 34 to generate compound image data. Here, the compound image data includes image data in which ultrasound image signals corresponding to a plurality of frames are superimposed and reversibly combined and image data in which ultrasound image signals corresponding to a plurality of frames are irreversibly combined so as to be one data item.

Under the control of the main body control unit 39, the display control unit 36 of the display-device-side processor 42 performs predetermined processing on the compound image data generated by the compound image data generation unit 35 and displays a compound image based on the compound image data on the display unit 37.

The main body control unit 39 controls each unit of the image display device 3 on the basis of the program stored in advance in the storage unit 41 and the operation of the user through the operation unit 40.

The display unit 37 displays the image generated by the display control unit 36 and includes a display device such as a liquid crystal display (LCD).

The operation unit 40 is used by the user to perform an input operation and can be configured to comprise, for example, a keyboard, a mouse, a trackball, a touch pad, and a touch panel.

The storage unit 41 stores, for example, an operation program for the image display device 3. The following can be used as the storage unit 41: a recording medium, such as a flash memory; a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory); or a sever.

In addition, the probe-side processor 25 including the transmitting unit 12, the receiving unit 13, the ultrasound transmission and reception control unit 15, the signal processing unit 16, the image processing unit 17, the header information attachment unit 18, the communication control unit 21, and the probe control unit 22 in the ultrasound probe 2 and the display-device-side processor 42 including the frame type determination unit 33, the combination determination unit 34, the compound image data generation unit 35, the display control unit 36, the communication control unit 38, and the main body control unit 39 in the image display device 3 are implemented by a central processing unit (CPU) and a control program for causing the CPU to perform various processes. However, the processors may be implemented by a field programmable gate array (FPGA), a digital signal processor (DSP), an application specific integrated circuit (ASIC), a graphics processing unit (GPU), other integrated circuits (ICs), or combinations thereof.

Some or all of the transmitting unit 12, the receiving unit 13, the ultrasound transmission and reception control unit 15, the signal processing unit 16, the image processing unit 17, the header information attachment unit 18, the communication control unit 21, and the probe control unit 22 of the probe-side processor 25 may be integrated into, for example, one CPU. Similarly, some or all of the frame type determination unit 33, the combination determination unit 34, the compound image data generation unit 35, the display control unit 36, the communication control unit 38, and the main body control unit 39 of the display-device-side processor 42 may be integrated into, for example, one CPU.

Next, the operation of the ultrasound system 1 according to Embodiment 1 of the invention will be described. Here, for the sake of explanation, it is assumed that a so-called spatial compound image obtained by combining N frame image information data items based on N different steering angle ranges is generated as the compound image generated in the ultrasound system 1. In this case, the transmitting and receiving unit 14 performs so-called steering scanning which gives a delay to driving signals supplied to the plurality of ultrasound transducers forming the transducer array 11 and reception signals from the plurality of ultrasound transducers to change the inclination of the scanning line and performs scanning.

First, in the ultrasound probe 2, under the control of the ultrasound transmission and reception control unit 15, the plurality of ultrasound transducers of the transducer array 11 transmit ultrasound beams according to the driving signals from the transmitting unit 12 of the transmitting and receiving unit 14, and each ultrasound transducer that has received ultrasound echoes from the subject outputs a reception signal which is an analog signal to the receiving unit 13. The amplification unit 27 amplifies the reception signal and the AD conversion unit 28 performs AD conversion on the reception signal to acquire reception data. The beam former 29 performs a reception focusing process on the reception data to generate a sound ray signal corresponding to each frame of an ultrasound image.

In this case, the ultrasound transmission and reception control unit 15 controls the transmitting and receiving unit 14 such that ultrasonic waves are transmitted and received in a plurality of steering angle ranges according to a predetermined transmission and reception sequence. For example, in a case in which ultrasonic waves are transmitted and received in three steering angle ranges as the N different steering angle ranges, the ultrasound transmission and reception control unit 15 can control the transmitting and receiving unit 14 such that ultrasonic waves are transmitted and received in the order of a first steering angle range, a second steering angle range, and a third steering angle range as the transmission and reception sequence. In this way, the beam former 29 generates a sound ray signal corresponding to each frame in a plurality of steering angle ranges.

The signal processing unit 16 of the frame image information data generation unit 20 performs attenuation correction according to the depth of a reflection position and an envelope detection process on the sound ray signals generated by the beam former 29 of the receiving unit 13 to generate signals which are tomographic image information related to the tissues in the subject. The image processing unit 17 performs raster conversion and various types of necessary image processing on the signals to generate, for example, ultrasound image signals F1 to F9 illustrated in FIG. 3 as the frame image information data.

Figure 3:
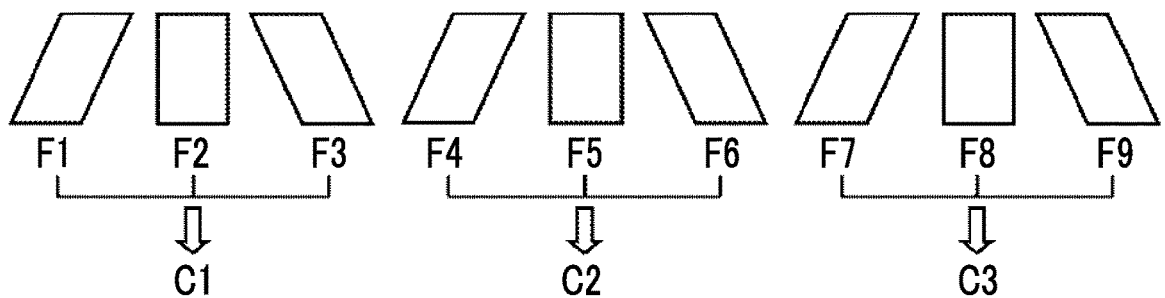
FIG. 3 is a diagram schematically illustrating an example of frame image information data according to Embodiment 1 of the invention.

In the example illustrated in FIG. 3, the ultrasound image signals F1 to F9 are generated in the order of the ultrasound image signals F1, F2, F3, . . . , F9 on the basis of three different steering angle ranges and the predetermined transmission and reception sequence. The ultrasound image signals F1, F4, and F7 correspond to the first steering angle range, the ultrasound image signals F2, F5, and F8 correspond to the second steering angle range, and the ultrasound image signals F3, F6, and F9 correspond to the third steering angle range. In this case, in the image display device 3, for example, compound image data items C1, C2, and C3 are generated on the basis of the ultrasound image signals F1 to F3, F4 to F6, and F7 to F9 corresponding to the three different steering angle ranges, respectively.

The header information attachment unit 18 attaches header information to the generated ultrasound image signals corresponding to the plurality of frames. For example, the header information attachment unit 18 can sequentially give, as header information, frame numbers to the ultrasound image signals F1 to F9 corresponding to the plurality of frames as illustrated in FIG. 3 in the order of the ultrasound image signals F1, F2, F3, . . . , F9. The ultrasound image signals corresponding to the plurality of frames to which the header information has been attached are transmitted to the wireless communication unit 19 of the ultrasound probe 2 and then wirelessly transmitted as transmission signals from the wireless communication unit 19 of the ultrasound probe 2 to the image display device 3.

The wireless communication unit 32 of the image display device 3 demodulates the plurality of transmission signals wirelessly transmitted from the wireless communication unit 19 of the ultrasound probe 2 into the ultrasound image signals corresponding to the plurality of frames. The frame type determination unit 33 of the display-device-side processor 42 determines the frame type of each of the demodulated ultrasound image signals corresponding to the plurality of frames.

In this case, for example, the frame type determination unit 33 determines the frame type, that is, whether the ultrasound image signals corresponding to the plurality of frames correspond to the first steering angle range, the second steering angle range, or the third steering angle range, on the basis of the frame numbers attached to the ultrasound image signals corresponding to the plurality of frames by the header information attachment unit 18 of the probe-side processor 25 and the predetermined transmission and reception sequence in the transmitting and receiving unit 14 of the probe-side processor 25. For example, the frame type determination unit 33 can determine that the ultrasound image signal F1 corresponds to the first steering angle range since the frame number of the ultrasound image signal F1 is "1", determine that the ultrasound image signal F2 corresponds to the second steering angle range since the frame number of the ultrasound image signal F2 is "2", and determine that the ultrasound image signal F3 corresponds to the third steering angle range since the frame number of the ultrasound image signal F3 is "3".

Figure 4:
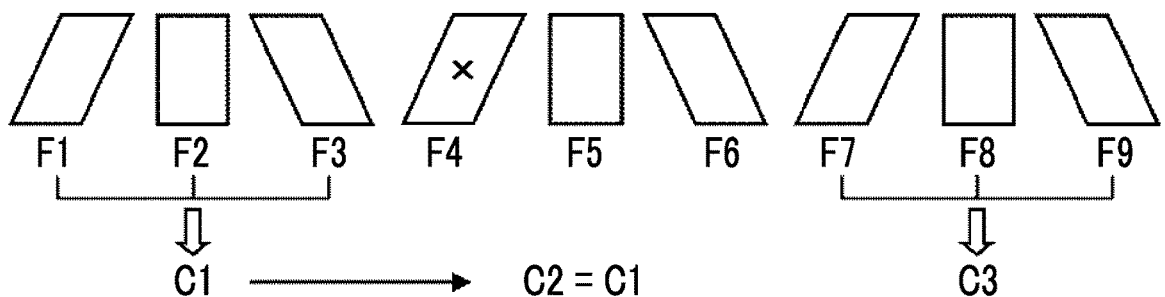
FIG. 4 is a diagram schematically illustrating an example of image combination according to Embodiment 1 of the invention.

The combination determination unit 34 of the display-device-side processor 42 determines whether or not to combine the ultrasound image signals on the basis of the frame types of the ultrasound image signals corresponding to the plurality of frames determined by the frame type determination unit 33. Here, for example, the combination determination unit 34 determines not to generate the compound image data C2, that is, not to combine the ultrasound image signals F4 to F6 in a case in which the ultrasound image signal F4, which corresponds to the first steering angle and is used for the generation of the compound image data C2, among the ultrasound image signals F1 to F9 is not normally wirelessly transmitted due to the deterioration of a wireless communication state, such as the interruption of the wireless communication between the wireless communication unit 19 of the ultrasound probe 2 and the wireless communication unit 32 of the image display device 3, as illustrated in FIG. 4. In addition, the combination determination unit 34 determines to combine the ultrasound image signals F1 to F3 and F7 to F9 in a case in which all of the ultrasound image signals F1 to F3 and F7 to F9 that are used to generate the compound image data items C1 and C3, respectively, are normally wirelessly transmitted, like the ultrasound image signals F1 to F3 and F7 to F9 illustrated in FIG. 4.

As such, in a case in which at least one ultrasound image signal among N frame image information data items used to generate one compound image data item, for example, the ultrasound image signals corresponding to three frames is not normally wirelessly transmitted, the combination determination unit 34 can determine not to combine the ultrasound image signals for generating the compound image data. In a case in which all of the N frame image information data items used to generate one compound image data item, for example, the ultrasound image signals corresponding to three frames are normally wirelessly transmitted, the combination determination unit 34 can determine to combine the ultrasound image signals for generating the compound image data. Therefore, the ultrasound image signals are combined only in a case in which normal compound image data is obtained.

Then, the compound image data generation unit 35 of the display-device-side processor 42 combines a plurality of ultrasound images determined to be combined by the combination determination unit 34 to generate compound image data. For example, as illustrated in FIG. 4, the compound image data generation unit 35 does not combine the ultrasound image signals F4 to F6, combines the ultrasound image signals F1 to F3 to generate the compound image data C1, and combines the ultrasound image signals F7 to F9 to generate the compound image data C3.

In a case in which the compound image data generation unit 35 generates the compound image data in this way, the display control unit 36 performs predetermined processing on the compound image data, and the display unit 37 displays a compound image based on the compound image data. In this case, for example, as illustrated in FIG. 4, instead of the compound image data C2 which has not been generated by the compound image data generation unit 35, a compound image based on the compound image data C1 that is before the compound image data C2 in time series is displayed on the display unit 37. That is, the display unit 37 displays the compound image based on the compound image data C1 until display is switched to the display of a compound image based on the compound image data C3. Therefore, the display unit 37 displays only the compound image based on the compound image data generated by the ultrasound image signals normally wirelessly transmitted by wireless communication.

As described above, according to the ultrasound system 1 of Embodiment 1 of the invention, the frame type determination unit 33 of the display-device-side processor 42 determines the frame types of the ultrasound image signals corresponding to a plurality of frames and the combination determination unit 34 determines to combine the ultrasound image signals on the basis of the frame types only in a case in which normal compound image data is obtained. The display unit 37 displays only the normal compound image. Therefore, it is possible to normally display the compound image regardless of the wireless communication state between the ultrasound probe 2 and the image display device 3.

In Embodiment 1, in a case in which even one of the ultrasound image signals used to generate the compound image data is not normally wirelessly transmitted as illustrated in FIG. 4, the combination determination unit 34 of the display-device-side processor 42 determines not to perform combination for generating the compound image data corresponding to the ultrasound image signal. However, the determination method in the combination determination unit 34 is not limited thereto.

Figure 5:
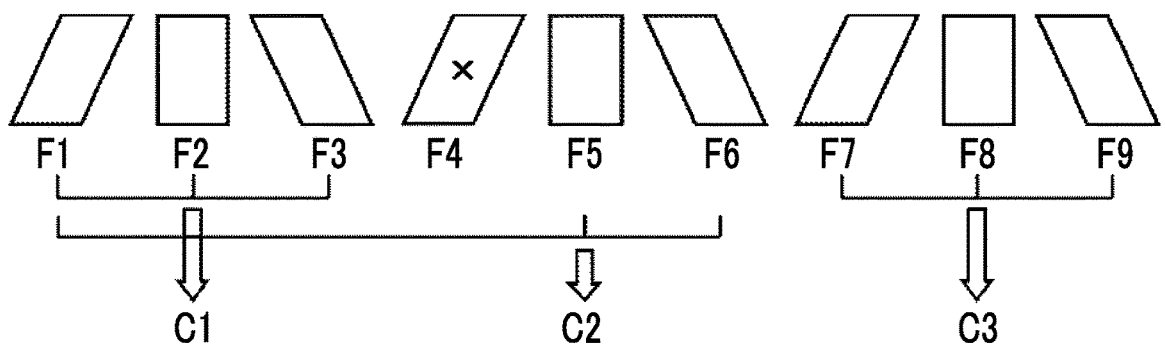
FIG. 5 is a diagram schematically illustrating another example of the image combination according to Embodiment 1 of the invention.

For example, in a case in which the ultrasound image signal F4 among the ultrasound image signals F4 to F6 used to generate the compound image data C2 is not normally wirelessly transmitted as illustrated in FIG. 5, the combination determination unit 34 determines to perform combination for generating the compound image data C2, using the ultrasound image signal F1, which has been acquired before the ultrasound image signal F4 in time series and corresponds to the same steering angle range as the ultrasound image signal F4, instead of the ultrasound image signal F4. In this case, the compound image data generation unit 35 combines the ultrasound image signals F1, F5, and F6 to generate the compound image data C2, and the compound images corresponding to the compound image data items C1 to C3 are sequentially displayed on the display unit 37.

In a case in which two of the ultrasound image signals F4 to F6 used to generate the compound image data C2, for example, the ultrasound image signals F4 and F5 are not normally wirelessly transmitted, the combination determination unit 34 determines to perform combination for generating the compound image data C2, using the ultrasound image signal F1 and the ultrasound image signal F2 instead of the ultrasound image signal F4 and the ultrasound image signal F5, respectively, which is not illustrated. In this case, the compound image data generation unit 35 combines the ultrasound image signals F1, F2, and F6 to generate the compound image data C2, and the compound images corresponding to the compound image data items C1 to C3 are sequentially displayed on the display unit 37.

In a case in which all of the ultrasound image signals F4 to F6 used to generate the compound image data C2 are not normally wirelessly transmitted, the combination determination unit 34 determines not to perform combination for generating the compound image data C2. In this case, the compound image data generation unit 35 generates only the compound image data items C1 and C3 among the compound image data items C1 to C3, and the display control unit 36 displays the compound images based on the compound image data items C1 and C3 on the display unit 37. In this case, instead of the compound image data C2 which has not been generated by the compound image data generation unit 35, the compound image based on the compound image data C1 is displayed on the display unit 37.

As such, in a case in which all of the ultrasound image signals used to generate one compound image data item are not normally wirelessly transmitted, the combination determination unit 34 can determine not to combine the ultrasound image signals for generating the compound image data. In a case in which some of the ultrasound image signals used to generate one compound image data item are normally wirelessly transmitted, the combination determination unit 34 can determine to combine the ultrasound image signals for generating the compound image data. In this case, it is also possible to normally display the compound image on the display unit 37.

In Embodiment 1, the header information attachment unit 18 of the probe-side processor 25 attaches, as the header information, frame numbers to the ultrasound image signals corresponding to the plurality of frames generated by the frame image information data generation unit 20. However, the header information is not limited thereto. For example, the header information attachment unit 18 can attach, as the header information, the generation time of each ultrasound image signal to the ultrasound image signals corresponding to the plurality of frames. In this case, the frame type determination unit 33 of the display-device-side processor 42 can determine the frame types of the ultrasound image signals corresponding to the plurality of frames on the basis of the attached generation time of each ultrasound image signal and the predetermined transmission and reception sequence in the transmitting and receiving unit 14 of the probe-side processor 25, as in the case in which the frame numbers are attached to the ultrasound image signals corresponding to the plurality of frames.

In addition, the header information attachment unit 18 can attach the frame type as the header information to the ultrasound image signal generated by the frame image information data generation unit 20. For example, in the example illustrated in FIG. 3, the header information attachment unit 18 attaches header information indicating the ultrasound image signals corresponding to the first steering angle range to the ultrasound image signals F1, F4, and F7, attaches header information indicating the ultrasound image signals corresponding to the second steering angle range to the ultrasound image signals F2, F5, and F8, and attaches header information indicating the ultrasound image signals corresponding to the third steering angle range to the ultrasound image signals F3, F6, and F9. In this case, the frame type determination unit 33 of the display-device-side processor 42 can determine the frame types of the ultrasound image signals corresponding to a plurality of frames according to the frame types attached by the header information attachment unit 18.

Further, the frame type determination unit 33 of the display-device-side processor 42 can acquire a reception time when the transmission signal wirelessly transmitted from the wireless communication unit 19 of the ultrasound probe 2 was received by the wireless communication unit 32 of the image display device 3 and can determine the frame types of the ultrasound image signals corresponding to a plurality of frames on the basis of the reception time and the predetermined transmission and reception sequence in the transmitting and receiving unit 14 of the probe-side processor 25.

In Embodiment 1, a so-called spatial compound image obtained by combining a plurality of frame image information data items based on a plurality of different steering angle ranges is generated as the compound image generated in the ultrasound system 1. However, the compound image is not limited thereto. For example, the frame image information data generation unit 20 may be provided with a Doppler processing unit that performs a quadrature detection process and a Fourier transform process on the sound ray signal generated by the receiving unit 13 to generate a Doppler waveform image signal, instead of the signal processing unit 16 and the image processing unit 17. The Doppler processing unit may generate a fundamental wave image signal and a harmonic image signal as the frame image information data. The compound image data generation unit 35 of the image display device 3 may generate a so-called compound harmonic image obtained by combining a fundamental wave image and a harmonic image as the compound image. This configuration is not illustrated.

In this case, the frame type determination unit 33 of the display-device-side processor 42 determines whether the ultrasound image signals corresponding to the plurality of frames generated by the frame image information data generation unit 20 are fundamental wave image signals or harmonic image signals, on the basis of the header information attached by the header information attachment unit 18 of the probe-side processor 25 and the predetermined transmission and reception sequence in the transmitting and receiving unit 14.

As described above, even in a case in which a compound harmonic image is generated as the compound image generated in the ultrasound system 1, the frame type determination unit 33 of the display-device-side processor 42 determines the frame types of the ultrasound image signals corresponding to a plurality of frames, the combination determination unit 34 determines to combine the ultrasound image signals on the basis of the frame types only in a case in which normal compound image data is obtained, and only a normal compound image is displayed on the display unit 37, as in the case in which the spatial compound image is generated. Therefore, it is possible to normally display the compound image regardless of the wireless communication state between the ultrasound probe 2 and the image display device 3.

In addition, for example, a so-called frequency compound image may be generated by combining ultrasound images corresponding to a plurality of different frequency bands on the basis of reception signals obtained by directing the transmitting unit 12 of the transmitting and receiving unit 14 to transmit ultrasound beams having a plurality of different frequency bands into the subject from the transducer array 11. For example, the transmitting unit 12 can transmit an ultrasound beam having a center frequency of 4 MHz and an ultrasound beam having a center frequency of 6 MHz into the subject from the transducer array 11. Then, for example, the quadrature detection process can be performed on the basis of the obtained reception signals to acquire an ultrasound reception signal corresponding to the center frequency of 4 MHz and an ultrasound reception signal corresponding to the center frequency of 6 MHz.

In this case, the frame type determination unit 33 of the display-device-side processor 42 determines whether the ultrasound image signals corresponding to the plurality of frames generated by the frame image information data generation unit 20 are signals corresponding to the center frequency of 4 MHz or signals corresponding to the center frequency of 6 MHz, on the basis of the header information attached by the header information attachment unit 18 of the probe-side processor 25 and the predetermined transmission and reception sequence in the transmitting and receiving unit 14.

As such, even in a case in which the frequency compound image is generated as the compound image generated in the ultrasound system 1, the frame type determination unit 33 of the display-device-side processor 42 determines the frame types of the ultrasound image signals corresponding to the plurality of frames, the combination determination unit 34 determines to combine the ultrasound image signals on the basis of the frame types only in a case in which normal compound image data is obtained, and only a normal compound image is displayed on the display unit 37, as in the case in which the spatial compound image is generated. Therefore, it is possible to normally display an image regardless of the wireless communication state between the ultrasound probe 2 and the image display device 3.

Further, for example, the frame image information data generation unit 20 of the probe-side processor 25 generates a compound image of a B-mode image and a color Doppler image as the compound image generated in the ultrasound system 1 in a case in which it includes a B-mode processing unit that generates a B-mode image signal corresponding to a so-called B-mode image and a color Doppler processing unit that generates a color Doppler image signal corresponding to a so-called color Doppler image, which is not illustrated.

In this case, the frame type determination unit 33 of the display-device-side processor 42 determines whether the ultrasound image signals corresponding to the plurality of frames generated by the frame image information data generation unit 20 are the B-mode image signals or the color Doppler image signals, on the basis of the header information attached by the header information attachment unit 18 of the probe-side processor 25 and the predetermined transmission and reception sequence in the transmitting and receiving unit 14.

As such, even in a case in which a compound image of a B-mode image and a color Doppler image is generated as the compound image generated in the ultrasound system 1, the frame type determination unit 33 of the display-device-side processor 42 determines the frame types of the ultrasound image signals corresponding to the plurality of frames, the combination determination unit 34 determines to combine the ultrasound image signals on the basis of the frame types only in a case in which normal compound image data is obtained, and only a normal compound image is displayed on the display unit 37, as in the case in which the spatial compound image is generated. Therefore, it is possible to normally display the compound image regardless of the wireless communication state between the ultrasound probe 2 and the image display device 3.

Figure 6:
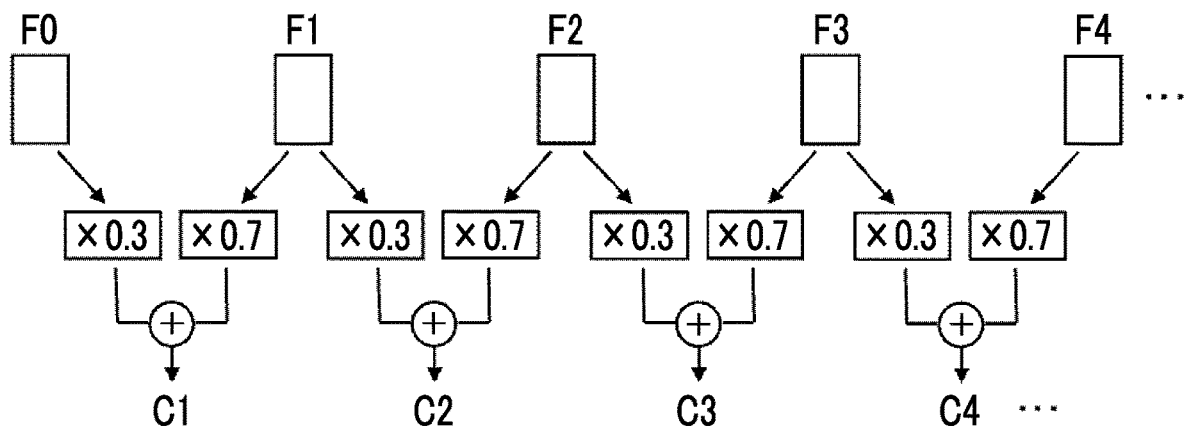
FIG. 6 is a diagram schematically illustrating an example of image combination according to a modification example of Embodiment 1 of the invention.

Further, it is known that compound images are sequentially generated by a so-called frame correlation (persistence) method which weights and adds a plurality of ultrasound image signals that are continuous in time series in order to make the movement of a moving image look smooth. For example, as illustrated in FIG. 6, in a case in which a compound image is generated on the basis of two ultrasound image signals that are continuous in time series, of two ultrasound image signals that are continuous in time series among the ultrasound image signals F0 to F4 generated in the order of the ultrasound image signals F0, F1, F2, F3, F4, . . . on the basis of the predetermined transmission and reception sequence, a signal obtained by multiplying a previous ultrasound image signal by a weight of 0.3 and a signal obtained by multiplying the latest ultrasound image signal by a weight of 0.7 can be added to generate compound image data C1. Similarly, compound image data items C2 to C4 can be sequentially generated from two ultrasound image signals that are continuous in time series.

A compound image based on a plurality of ultrasound image signals that are continuous in time series may be generated as the compound image generated in the ultrasound system 1 by the frame correlation.

In this case, the header information attachment unit 18 of the probe-side processor 25 can attach, as the header information, consecutive frame numbers or the generation time of each ultrasound image signal to the ultrasound image signals corresponding to the plurality of frames generated by the frame image information data generation unit 20, and the frame type determination unit 33 can determine whether or not the ultrasound image signals are continuous in time series without being missed on the basis of the header information attached to the ultrasound image signals. That is, the frame type determination unit 33 can determine whether the ultrasound image signals are continuous in time series from the previous ultrasound image signal or the previous ultrasound image signal is missed as the frame type on the basis of the header information attached to the ultrasound image signals.

Figure 7:
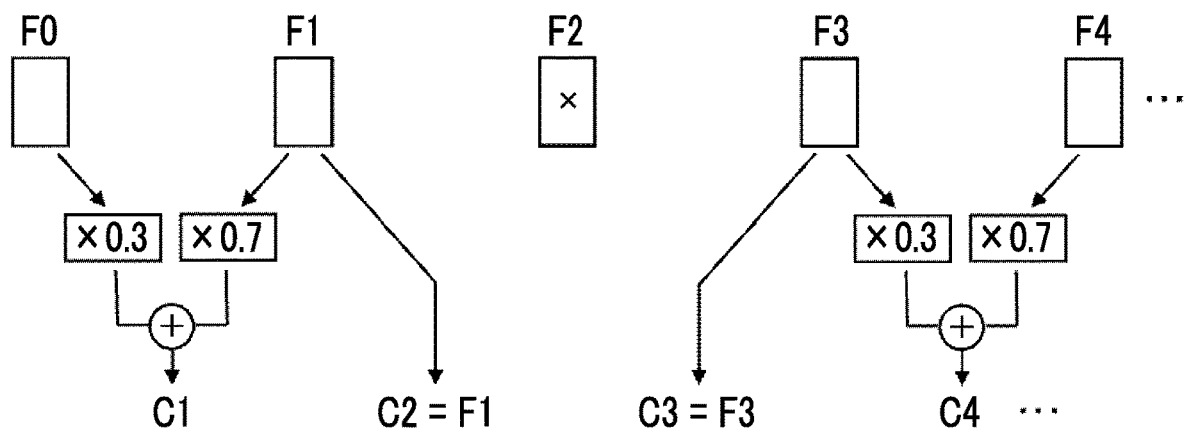
FIG. 7 is a diagram schematically illustrating another example of the image combination according to the modification example of Embodiment 1 of the invention.

For example, in the generation of a compound image on the basis of two ultrasound image signals that are continuous in time series, in a case in which the ultrasound image signal F2 is determined to be missed without being normally wirelessly transmitted from the ultrasound probe 2 as illustrated in FIG. 7, the combination determination unit 34 determines not to perform combination for generating the compound image data C2 and combination for generating the compound image data C3, using the ultrasound image signal F2. The compound image data generation unit 35 can generate a series of the compound image data items C1 to C4, using the ultrasound image signal F1 immediately before the ultrasound image signal F2 as the compound image data C2 and the ultrasound image signal F3 immediately after the ultrasound image signal F2 as the compound image data C3 without any change.

As such, even in a case in which a compound image based on a plurality of ultrasound image signals that are continuous in time series is generated by frame correlation as the compound image generated in the ultrasound system 1, the frame type determination unit 33 of the display-device-side processor 42 determines the frame types of the ultrasound image signals corresponding to a plurality of frames, the combination determination unit 34 determines to combine the ultrasound image signals on the basis of the frame types only in a case in which normal compound image data is obtained, and only a normal compound image is displayed on the display unit 37. Therefore, it is possible to normally display the compound image regardless of the wireless communication state between the ultrasound probe 2 and the image display device 3.

The example in which a compound image is generated by the frame correlation method on the basis of two ultrasound image signals that are continuous in time series has been described. However, a compound image may be generated on the basis of three or more ultrasound image signals that are continuous in time series. For example, in a case in which a compound image is generated on the basis of three ultrasound image signals that are continuous in time series, compound image data can be generated by adding a signal obtained by multiplying the oldest generated ultrasound image signal among the three ultrasound image signals that are continuous in time series by a weight of 0.1, a signal obtained by multiplying the previous ultrasound image signal by a weight of 0.3, and a signal obtained by multiplying the latest ultrasound image signal by a weight of 0.6.

Embodiment 2

In Embodiment 1, the header information attachment unit 18 of the probe-side processor 25 attaches the header information to the ultrasound image signals corresponding to a plurality of frames, and the frame type determination unit 33 of the display-device-side processor 42 determines the frame types of the ultrasound image signals corresponding to the plurality of frames on the basis of the header information and the transmission and reception sequence in the transmitting and receiving unit 14 of the probe-side processor 25. However, the frame types may be determined by analyzing the ultrasound image signals corresponding to the plurality of frames.

Figure 8:
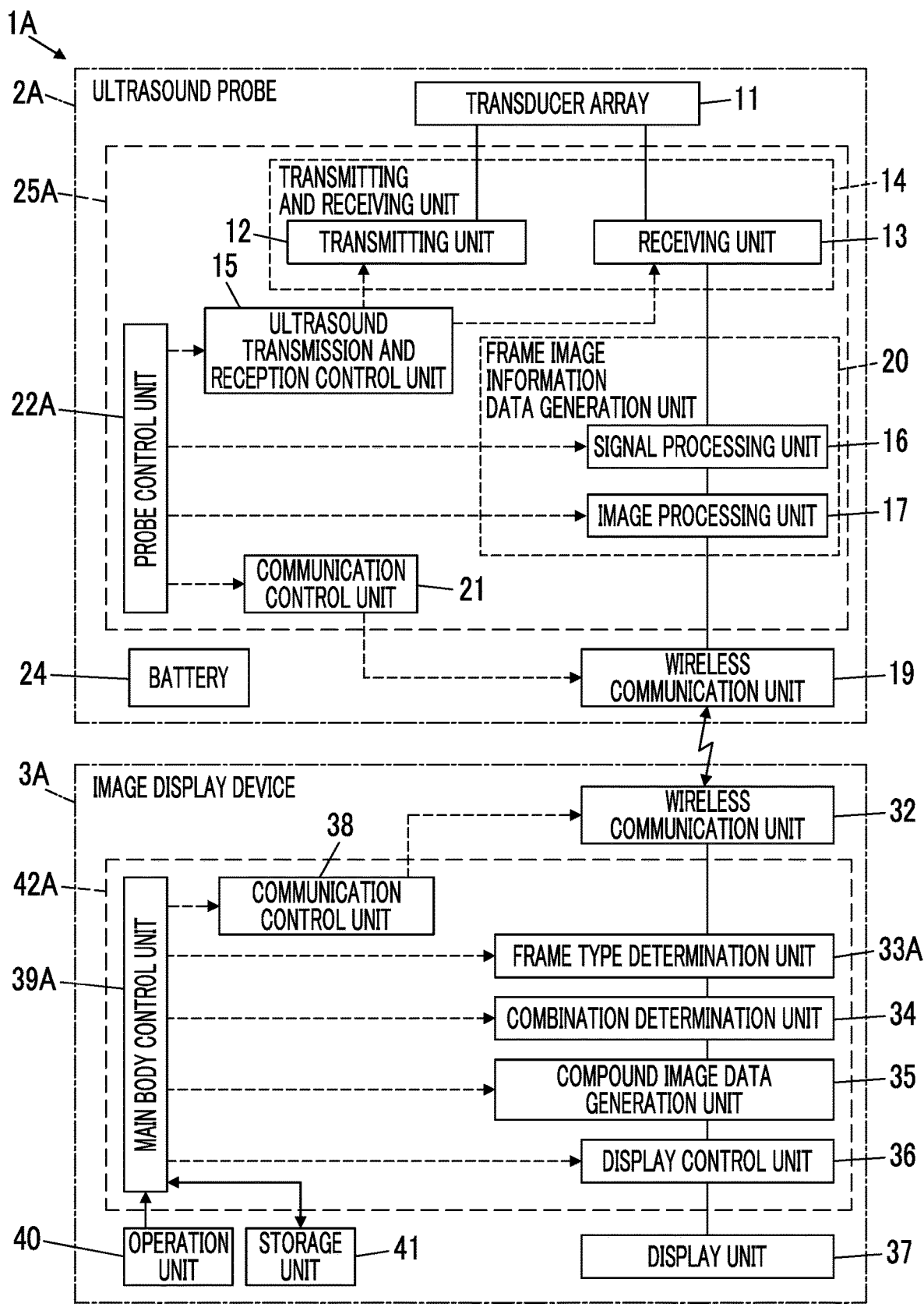
FIG. 8 is a block diagram illustrating a configuration of an ultrasound system according to Embodiment 2 of the invention.

As illustrated in FIG. 8, an ultrasound system 1A according to Embodiment 2 comprises an ultrasound probe 2A and an image display device 3A. The ultrasound probe 2A is different from the ultrasound probe 2 according to Embodiment 1 illustrated in FIG. 1 in that the header information attachment unit 18 is removed and a probe control unit 22A is provided instead of the probe control unit 22. In addition, the image display device 3A is different from the image display device 3 according to Embodiment 1 illustrated in FIG. 1 in that it comprises a frame type determination unit 33A instead of the frame type determination unit 33 and comprises a main body control unit 39A instead of the main body control unit 39.

In the ultrasound probe 2A, the image processing unit 17 is directly connected to the wireless communication unit 19. The probe control unit 22A is connected to the ultrasound transmission and reception control unit 15, the signal processing unit 16, the image processing unit 17, and the communication control unit 21. A probe-side processor 25A is configured by the transmitting and receiving unit 14, the ultrasound transmission and reception control unit 15, the frame image information data generation unit 20, the communication control unit 21, and the probe control unit 22A.

Further, in the image display device 3A, the frame type determination unit 33A is connected to the wireless communication unit 32, and the combination determination unit 34 is connected to the frame type determination unit 33A. Further, the main body control unit 39A is connected to the frame type determination unit 33A, the combination determination unit 34, the compound image data generation unit 35, the display control unit 36, the communication control unit 38, the operation unit 40, and the storage unit 41. Furthermore, a display-device-side processor 42A is configured by the frame type determination unit 33A, the combination determination unit 34, the compound image data generation unit 35, the display control unit 36, the communication control unit 38, and the main body control unit 39A.

The wireless communication unit 19 of the ultrasound probe 2A modulates a carrier on the basis of the ultrasound image signals corresponding to a plurality of frames generated by the image processing unit 17 of the frame image information data generation unit 20 to generate transmission signals and sequentially wirelessly transmits the generated transmission signals to the image display device 3A.

The wireless communication unit 32 of the image display device 3A demodulates the transmission signals wirelessly transmitted from the wireless communication unit 19 of the ultrasound probe 2A to acquire the ultrasound image signals corresponding to the plurality of frames, and transmits the demodulated ultrasound image signals corresponding to the plurality of frames to the frame type determination unit 33A.

Figure 9:
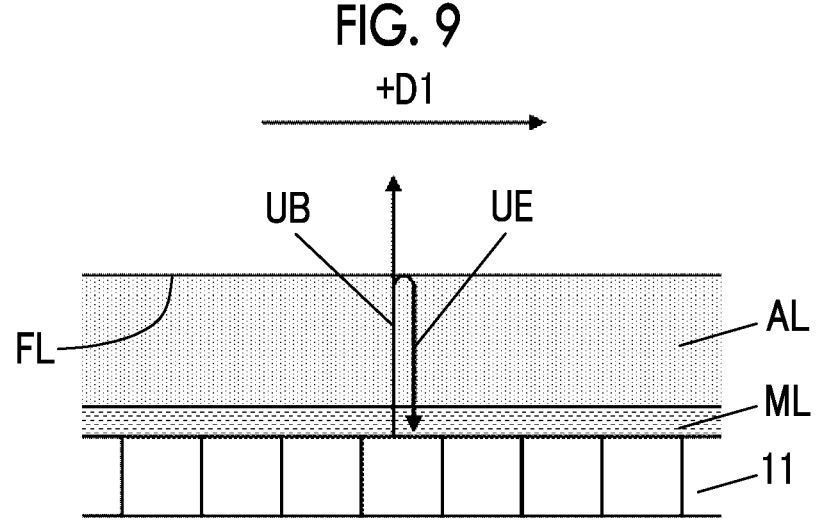
FIG. 9 is a diagram schematically illustrating an ultrasound echo reflected by a front surface of an acoustic lens in Embodiment 2 of the invention.

Here, as illustrated in FIG. 9, an acoustic matching layer ML is stacked on the transducer array 11 and an acoustic lens AL is stacked on the acoustic matching layer ML. For the sake of description, in the following description, it is assumed that a plurality of ultrasound transducers forming the transducer array 11 are arranged in a +D1 direction and a direction opposite to the +D1 direction is referred to as a −D1 direction.

The acoustic matching layer ML is a layer for matching acoustic impedance between the transducer array 11 and an imaging target such as a subject.

Further, the acoustic lens AL is for normally focusing the ultrasound beams transmitted from the transducer array 11 on a scanning line and normally receiving the ultrasound echoes emitted from the focus on the scanning line. For example, a silicon-based resin, such as a millable silicon rubber or a liquid silicon rubber, a butadiene-based resin, or a polyurethane-based resin is used as the acoustic lens AL.

As illustrated in FIG. 9, in a case in which ultrasound beams UB are transmitted from the transducer array 11, the ultrasound beams UB travel through the acoustic matching layer ML and the acoustic lens AL. For example, some of the ultrasound beams UB are reflected from a front surface FL of the acoustic lens AL and are incident on the transducer array 11 as ultrasound echoes UE. Therefore, a predetermined region of a shallow portion in the ultrasound image signals corresponding to the plurality of frames generated by the frame image information data generation unit 20 includes a signal corresponding to the ultrasound echo UE emitted from the front surface FL of the acoustic lens AL. Here, it is assumed that the front surface FL of the acoustic lens AL is a surface that is opposite to the surface of the acoustic lens AL which comes into contact with the acoustic matching layer ML and comes into contact with the body surface of the subject in a case in which an ultrasound diagnosis is performed.

The frame type determination unit 33A of the display-device-side processor 42A analyzes data corresponding to the predetermined region of the shallow portion in the ultrasound image signals transmitted from the wireless communication unit 32 of the image display device 3A to determine the frame types of the ultrasound image signals corresponding to the plurality of frames.

Here, in a case in which the transmitting and receiving unit 14 performs ultrasound steering scanning and ultrasound beams are transmitted from the transducer array 11, the timing when a driving signal is supplied from the transmitting unit 12 to each of the ultrasound transducers forming the transducer array 11, that is, the transmission timing of each ultrasound transducer is set such that there is a difference between the transmission timings, according to the steering angle in the steering scanning. Therefore, there is a difference in the time when the ultrasonic waves emitted from each ultrasound transducer are reflected by the front surface FL of the acoustic lens AL, according to the steering angle. In addition, there is a difference in the time when each ultrasound transducer receives the ultrasound echoes UE reflected from the front surface FL of the acoustic lens AL.

Therefore, for example, in a case in which a spatial compound image is generated in the ultrasound system 1A, the frame type determination unit 33A can determine, as the frame type, which steering angle range each ultrasound image signal corresponds to by analyzing the ultrasound image signals corresponding to the plurality of frames transmitted from the wireless communication unit 32 of the image display device 3A to acquire the time when each ultrasound transducer receives the ultrasound echo corresponding to a predetermined region of the shallow portion.

For example, in a case in which the steering angle in the steering scanning is 0 degrees, that is, the direction of the scanning line is perpendicular to the +D1 direction which is the arrangement direction of the plurality of ultrasound transducers forming the transducer array 11, the timings when the ultrasound transducers transmit ultrasonic waves are equal to each other and the timings when the ultrasound transducers receive the ultrasound echoes UE from the front surface FL of the acoustic lens AL are equal to each other. Therefore, the frame type determination unit 33A can analyze the ultrasound image signals and determine the analyzed ultrasound image signals as signals corresponding to the steering angle range in which the steering angle is 0 degrees in a case in which the timings when the ultrasound transducers receive the ultrasound echoes UE from the front surface FL of the acoustic lens AL are equal to each other.

Further, for example, in a case in which the steering angle in the steering scanning is inclined in the +D1 direction, the ultrasound transducer located closer to the +D1 direction in the transducer array 11 transmits ultrasonic waves later. In addition, the ultrasound transducer located closer to the +D1 direction receives the ultrasound echo UE from the front surface FL of the acoustic lens AL later. Therefore, the frame type determination unit 33A can analyze the ultrasound image signals and determine the analyzed ultrasound image signals as signals corresponding to the steering angle inclined in the +D1 direction in a case in which the ultrasound transducer located closer to the +D1 direction receives the ultrasound echo UE from the front surface FL of the acoustic lens AL later.

Further, for example, in a case in which the steering angle in the steering scanning is inclined in the −D1 direction, the ultrasound transducer located closer to the −D1 direction in the transducer array 11 transmits ultrasonic waves later. In addition, the ultrasound transducer located closer to the −D1 direction receives the ultrasound echo UE from the front surface FL of the acoustic lens AL later. Therefore, the frame type determination unit 33A can analyze the ultrasound image signals and determine the analyzed ultrasound image signals as signals corresponding to the steering angle inclined in the −D1 direction in a case in which the ultrasound transducer located closer to the −D1 direction receives the ultrasound echo UE from the front surface FL of the acoustic lens AL later.

The combination determination unit 34 of the display-device-side processor 42A determines whether or not to combine the ultrasound image signals on the basis of the frame type of each ultrasound image signal determined by the frame type determination unit 33A and the predetermined transmission and reception sequence in the transmitting and receiving unit 14 of the probe-side processor 25A.

The compound image data generation unit 35 of the display-device-side processor 42A combines the ultrasound image signals corresponding to the plurality of frames determined to be combined by the combination determination unit 34 to generate compound image data.

The display control unit 36 of the display-device-side processor 42A performs predetermined processing on the compound image data generated by the compound image data generation unit 35 to generate an image that can be displayed on the display unit 37 and displays a compound image on the display unit 37.

As described above, according to the ultrasound system 1A of Embodiment 2 of the invention, even in a case in which the frame type determination unit 33A analyzes the ultrasound image signals corresponding to a plurality of frames generated by the frame image information data generation unit 20 and determines the frame type of each ultrasound image signal, only a normal compound image is displayed on the display unit 37, as in the ultrasound system 1 according to Embodiment 1. Therefore, it is possible to normally display the compound image regardless of the wireless communication state between the ultrasound probe 2A and the image display device 3A.

In Embodiment 2, a spatial compound image is generated in the ultrasound system 1A. However, the aspect of Embodiment 2 can also be applied to a case in which a compound harmonic image, a frequency compound image, a compound image of a B-mode image and a color Doppler image, and the like are generated.

Here, the compound harmonic image is generated by combining a fundamental wave image signal and a harmonic image signal. However, in general, the intensity of an ultrasound echo corresponding to the fundamental wave image signal is higher than the intensity of an ultrasound echo corresponding to the harmonic image signal. Therefore, for example, the frame type determination unit 33A of the display-device-side processor 42A can determine whether each ultrasound image signal is the fundamental wave image signal or the harmonic image signal by analyzing the ultrasound image signals corresponding to the plurality of frames transmitted from the wireless communication unit 32 of the image display device 3A to acquire the intensity of the ultrasound image signal corresponding to the predetermined region of the shallow portion including the ultrasound echo UE reflected from the front surface FL of the acoustic lens AL.

Further, the frequency compound image is generated by combining the ultrasound image signals generated on the basis of the ultrasound beams having different center frequencies and the ultrasound echoes. Therefore, for example, the frame type determination unit 33A can determine which center frequency each ultrasound image signal corresponds to by analyzing the ultrasound image signals corresponding to the plurality of frames transmitted from the wireless communication unit 32 of the image display device 3A to acquire the center frequency that corresponds to the ultrasound image signal corresponding to the predetermined region of the shallow portion including the ultrasound echo UE reflected from the front surface FL of the acoustic lens AL.

In general, the number of ultrasound pulses per scanning line emitted from the transducer array 11 in order to generate a color Doppler image signal is greater than the number of ultrasound pulses emitted from the transducer array 11 in order to generate a B-mode image signal. The length of a received echo from the same reflector, that is, the same reflection position in the color Doppler image signal is larger than the length of a received echo from the same reflector in the B-mode image signal. Therefore, for example, the frame type determination unit 33A can determine whether each ultrasound image signal is a B-mode image signal or a color Doppler image signal by analyzing the ultrasound image signals corresponding to the plurality of frames transmitted from the wireless communication unit 32 of the image display device 3A and comparing the lengths of the received echoes from the same reflector, that is, the same reflection position in the ultrasound image signals corresponding to the predetermined region of the shallow portion including the ultrasound echo UE reflected from the front surface FL of the acoustic lens AL.

Embodiment 3

Figure 10:
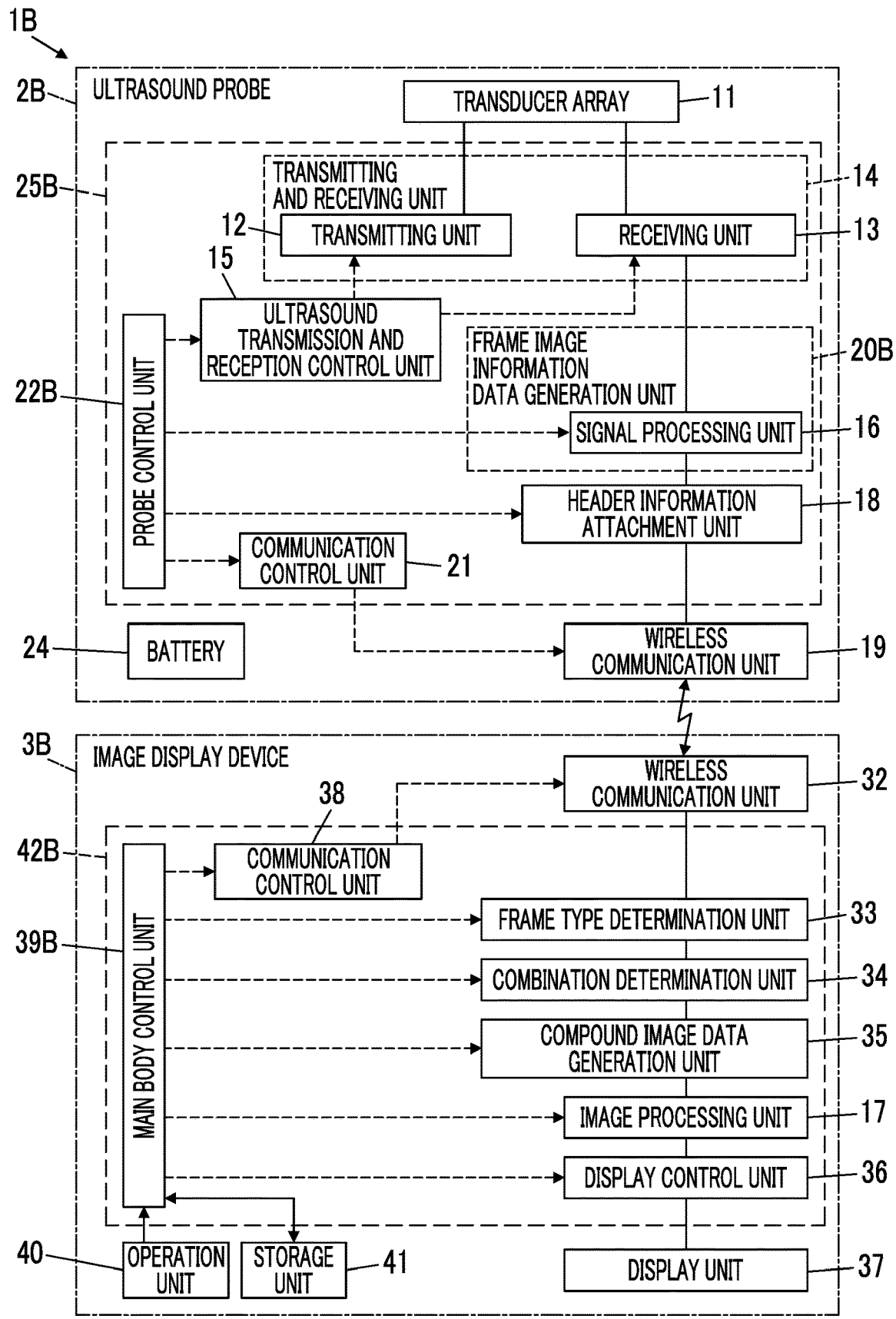
FIG. 10 is a block diagram illustrating a configuration of an ultrasound system according to Embodiment 3 of the invention.

As illustrated in FIG. 10, an ultrasound system 1B according to Embodiment 3 comprises an ultrasound probe 2B and an image display device 3B. The ultrasound probe 2B is different from the ultrasound probe 2 according to Embodiment 1 illustrated in FIG. 1 in that the image processing unit 17 is removed and a probe control unit 22B is provided instead of the probe control unit 22. In addition, the image display device 3B is different from the image display device 3 according to Embodiment 1 illustrated in FIG. 1 in that the image processing unit 17 is added and a main body control unit 39B is provided instead of the main body control unit 39. The image processing unit 17 in the image display device 3B is the same as the image processing unit 17 in Embodiment 1 illustrated in FIG. 1.

In the ultrasound probe 2B, the header information attachment unit 18 is connected to the signal processing unit 16, and the signal processing unit 16 forms a frame image information data generation unit 20B. The probe control unit 22B is connected to the ultrasound transmission and reception control unit 15, the signal processing unit 16, the header information attachment unit 18, and the communication control unit 21. Further, a probe-side processor 25B is configured by the transmitting and receiving unit 14, the ultrasound transmission and reception control unit 15, the signal processing unit 16, the header information attachment unit 18, the communication control unit 21, and the probe control unit 22B.

In the image display device 3B, the image processing unit 17 is connected to the compound image data generation unit 35, and the main body control unit 39B is connected to the image processing unit 17, the frame type determination unit 33, the combination determination unit 34, the compound image data generation unit 35, the display control unit 36, the communication control unit 38, the operation unit 40, and the storage unit 41. Furthermore, a display-device-side processor 42B is configured by the image processing unit 17, the frame type determination unit 33, the combination determination unit 34, the compound image data generation unit 35, the display control unit 36, the communication control unit 38, and the main body control unit 39B.

The signal processing unit 16 of the frame image information data generation unit 20B corrects the attenuation of the sound ray signal generated by the beam former 29 caused by a propagation distance according to the depth of the position where the ultrasonic waves are reflected and performs an envelope detection process on sound ray signal to generate, as a plurality of frame image information data items, signals that are tomographic image information of a plurality of frames related to the tissues in the subject for each frame unit.

The header information attachment unit 18 of the probe-side processor 25B attaches header information, such as frame numbers, to the signals corresponding to the plurality of frames generated by the signal processing unit 16 and transmits the signals to the wireless communication unit 19 of the ultrasound probe 2B.

The wireless communication unit 19 of the ultrasound probe 2B modulates a carrier on the basis of the signals corresponding to the plurality of frames transmitted from the header information attachment unit 18 to generate transmission signals and wirelessly transmits the generated transmission signals to the image display device 3B.

The wireless communication unit 32 of the image display device 3B demodulates the transmission signals wirelessly transmitted from the wireless communication unit 19 of the ultrasound probe 2B and outputs the signals subjected to the envelope detection process to the frame type determination unit 33 of the display-device-side processor 42B.

The frame type determination unit 33 of the display-device-side processor 42B determines the frame types of the signals corresponding to the plurality of frames output from the wireless communication unit 32 of the image display device 3B, on the basis of the header information attached by the header information attachment unit 18 of the probe-side processor 25B and the predetermined transmission and reception sequence in the transmitting and receiving unit 14 of the probe-side processor 25B.

The combination determination unit 34 of the display-device-side processor 42B determines whether or not to combine the signals corresponding to the plurality of frames subjected to the envelope detection process, on the basis of the frame types determined by the frame type determination unit 33.

The compound image data generation unit 35 of the display-device-side processor 42B combines the signals corresponding to the plurality of frames subjected to the envelope detection process, which have been determined to be combined by the combination determination unit 34, to generate compound image data. Therefore, it is possible to generate a compound image signal using only the signals normally wirelessly transmitted from the ultrasound probe 2B to the image display device 3B.

The image processing unit 17 of the display-device-side processor 42B raster-converts the compound image data generated by the compound image data generation unit 35 into an image signal following a general television signal scanning method and performs various types of necessary image processing, such as brightness correction, gradation correction, sharpness correction, and color correction, on the image signal. The image processing unit 17 transmits the processed compound image data to the display control unit 36 of the display-device-side processor 42B.

The display control unit 36 of the display-device-side processor 42B performs predetermined processing on the compound image data transmitted from the image processing unit 17 and displays a compound image based on the compound image data on the display unit 37 under the control of the main body control unit 39B.

As described above, according to the ultrasound system 1B of Embodiment 3, similarly to the ultrasound system 1 according to Embodiment 1, even in a case in which the image processing unit 17 is not provided in the ultrasound probe 2B, but is provided in the image display device 3B, the frame type determination unit 33 of the display-device-side processor 42B determines the frame types of the signals corresponding to a plurality of frames subjected to the envelope detection process, and the combination determination unit 34 determines whether or not to combine the signals subjected to the envelope detection on the basis of the frame types only in a case in which normal compound image data is obtained. Then, only a normal compound image is displayed on the display unit 37. Therefore, it is possible to normally display the compound image regardless of the wireless communication state between the ultrasound probe 2B and the image display device 3B.

In the above-described Embodiments 1 and 2, the ultrasound image signals which have been subjected to attenuation correction and the envelope detection process by the signal processing unit 16 of the frame image information data generation unit 20 and then subjected to raster conversion by the image processing unit 17 are wirelessly transmitted as the image information data from the wireless communication unit 19 to the image display device 3 and the image display device 3A. In addition, in Embodiment 3, the signals which have been subjected to attenuation correction and the envelope detection process by the signal processing unit 16 of the frame image information data generation unit 20B are wirelessly transmitted as the image information data from the wireless communication unit 19 to the image display device 3B. As such, it is preferable that the image information data wirelessly transmitted from the ultrasound probes 2, 2A, and 2B to the image display devices 3, 3A, and 3B is a signal after detection. However, the image information data is not limited to the signal after detection.

In the image display devices 3, 3A, and 3B according to the above-described Embodiments 1 to 3, a touch sensor may be combined with the display unit 37 and may be used as the operation unit 40. In a case in which the image display devices 3, 3A, and 3B are configured in this way, they are also very effective for outdoor diagnosis during, for example, emergency treatment.

EXPLANATION OF REFERENCES 1, 1A, 1B: ultrasound system
2, 2A, 2B: ultrasound probe
3, 3A, 3B: image display device
11: transducer array
12: transmitting unit
13: receiving unit
14: transmitting and receiving unit
15: ultrasound transmission and reception control unit
16: signal processing unit
17: image processing unit
18: header information attachment unit
19, 32: wireless communication unit
20, 20B: frame image information data generation unit
21, 38: communication control unit
22, 22A, 22B: probe control unit
24: battery
25, 25A, 25B: probe-side processor
27: amplification unit
28: AD conversion unit
29: beam former
33: frame type determination unit
34: combination determination unit
35: compound image data generation unit
36: display control unit
37: display unit
39, 39A, and 39B: main body control unit
40: operation unit
41: storage unit
42, 42A, 42B: display-device-side processor
AL: acoustic lens
C1, C2, C3, C4: compound image data
F0 to F9: ultrasound image signal
FL: front surface
ML: acoustic matching layer
UB: ultrasound beam
UE: ultrasound echo

What is claimed is:

1. An ultrasound system comprising:
an ultrasound probe and an image display device that are wirelessly connected to each other,
wherein the image display device is configured to display a compound image based on a plurality of frame image information data items generated by the ultrasound probe, where the frame image information data is a signal obtained by performing attenuation correction according to a depth of a reflection position of the ultrasonic waves and an envelope detection process on a sound ray signal, or an ultrasound image signal obtained by performing attenuation correction according to a depth of a reflection position of the ultrasonic waves and an envelope detection process on the sound ray signal and converting the sound ray signal according to a predetermined image display method,
the ultrasound probe includes:
a transducer array;
a processor configured to:
perform transmission and reception of ultrasonic waves based on a transmission and reception sequence using the transducer array to generate the sound ray signal, and
generate the plurality of frame image information data items based on the sound ray signal; and
a wireless communication device configured to sequentially wirelessly transmit the plurality of frame image information data items generated by the processor in the ultrasound probe to the image display device, and
the image display device includes:
a monitor;
a processor configured to:
determine a steering angle range of each of the plurality of frame image information data items wirelessly transmitted through the wireless communication device of the ultrasound probe,
determine to combine the plurality of frame image information data items corresponding to a plurality of images having different steering angle ranges, in a case where frame image information data items corresponding to all of the steering angles needed to compose one compound image data are received from the ultrasound probe,
determine not to combine the plurality of frame image information data items, in a case where only a part of the frame image information data items corresponding to all of the steering angles needed to compose the one compound image data are received from the ultrasound probe,
once the plurality of frame image information data items are determined to be combined,
combine the plurality of frame image information data items corresponding to the plurality of images having different steering angle ranges to generate the compound image data, and
display on the monitor the compound image based on the compound image data, and
once the plurality of frame image information data items are determined not to be combined,
stop combining the plurality of frame image information data items, and
continue to display on the monitor the latest compound image which has already been generated and displayed on the monitor.

2. The ultrasound system according to claim 1,
wherein the processor in the ultrasound probe is further configured to attach header information to each of the plurality of frame image information data items, and
the processor in the image display device is further configured to determine the steering angle range of each of the plurality of frame image information data items based on the header information.

3. The ultrasound system according to claim 2,
wherein the header information includes frame numbers that are sequentially given to the plurality of frame image information data items, and
the processor in the image display device is further configured to determine the steering angle ranges based on the frame numbers of the plurality of frame image information data items and the transmission and reception sequence in the processor in the ultrasound probe.

4. The ultrasound system according to claim 2,
wherein the header information includes a generation time of each of the plurality of frame image information data items by the processor in the ultrasound probe, and
the processor in the image display device is further configured to determine the steering angle ranges based on the generation time of each of the plurality of frame image information data items and the transmission and reception sequence in the processor in the ultrasound probe.

5. The ultrasound system according to claim 2,
wherein the header information includes the steering angle range of each of the plurality of frame image information data items, and
the processor in the image display device is further configured to read the steering angle range from the header information to determine the steering angle range.

6. The ultrasound system according to claim 1,
wherein the processor in the image display device is further configured to analyze each of the frame image information data items to determine the steering angle range of the frame image information data.

7. The ultrasound system according to claim 6,
wherein the processor in the image display device is further configured to analyze data corresponding to a predetermined region of a shallow portion in the frame image information data to determine the steering angle range of the frame image information data.

8. The ultrasound system according to claim 7,
wherein the ultrasound probe includes an acoustic lens, and
the data corresponding to the predetermined region is data generated based on an ultrasound echo obtained by reflection of the ultrasonic waves transmitted from the transducer array from a front surface of the acoustic lens.

9. The ultrasound system according to claim 1,
wherein the processor in the image display device is further configured to weight and add a plurality of frame image information data items that are continuous in time series to generate the compound image data.

10. The ultrasound system according to claim 2,
wherein the processor in the image display device is further configured to weight and add a plurality of frame image information data items that are continuous in time series to generate the compound image data.

11. The ultrasound system according to claim 1,
wherein the processor in the ultrasound probe is further configured to direct the transducer array to transmit the ultrasonic waves, and generate the sound ray signal based on a reception signal acquired by the transducer array.

12. A method for controlling an ultrasound system which includes an ultrasound probe and an image display device wirelessly connected to each other and in which the image display device is configured to display a compound image based on a plurality of frame image information data items generated by the ultrasound probe, where the frame image information data is a signal obtained by performing attenuation correction according to a depth of a reflection position of the ultrasonic waves and an envelope detection process on a sound ray signal, or an ultrasound image signal obtained by performing attenuation correction according to a depth of a reflection position of the ultrasonic waves and an envelope detection process on the sound ray signal and converting the sound ray signal according to a predetermined image display method, the method comprising:
  performing transmission and reception of ultrasonic waves based on a transmission and reception sequence using a transducer array of the ultrasound probe to generate the sound ray signal;
  generating the plurality of frame image information data items based on the generated sound ray signal;
  sequentially wirelessly transmitting the plurality of generated frame image information data items from the ultrasound probe to the image display device;
  determining a steering angle range of each of the plurality of frame image information data items wirelessly transmitted from the ultrasound probe in the image display device;
  determining to combine the plurality of frame image information data items corresponding to a plurality of images having different steering angle ranges, in a case where frame image information data items corresponding to all of the steering angles needed to compose one compound image data are received from the ultrasound probe;
  determining not to combine the plurality of frame image information data items, in a case where only a part of the frame image information data items corresponding to all of the steering angles needed to compose the one compound image data are received from the ultrasound probe;
  once the plurality of frame image information data items are determined to be combined,
  combining the plurality of frame image information data items corresponding to the plurality of images having different steering angle ranges to generate the compound image data; and
  displaying on a monitor the compound image based on the compound image data; and
  once the plurality of frame image information data items are determined not to be combined,
  stopping combining the plurality of frame image information data items; and
  continuing to display on the monitor the latest compound image which has already been generated and displayed on the monitor.

* * * * *

UNITED STATES PATENT AND TRADEMARK OFFICE
CERTIFICATE OF CORRECTION

PATENT NO. : 11,766,241 B2
APPLICATION NO. : 17/062692
DATED : September 26, 2023
INVENTOR(S) : Yukiya Miyachi It is certified that error appears in the above-identified patent and that said Letters Patent is hereby corrected as shown below:

On the Title Page

Item (54) and in the Specification Column 1, Lines 1-8 ULTRASOUND SYSTEM IN WHICH AN ULTRASOUND PROBE AND A DISPLAY DEVICE ARE WIRELESSLY CONNECTED WITH EACH OTHER AND METHOD FOR CONTROLLING ULTRASOUND SYSTEM IN WHICH AN ULTRASOUND PROBE AND A DISPLAY DEVICE ARE WIRELESSLY CONNECTED WITH EACH OTHER Should be corrected to be:
ULTRASOUND SYSTEM AND METHOD FOR COMPOUNDING ULTRASOUND SIGNALS BASED ON STEERING ANGLE RANGES Signed and Sealed this
Twenty-eighth Day of November, 2023

Katherine Kelly Vidal
*Director of the United States Patent and Trademark Office*